(12) United States Patent
Kurahashi et al.

(10) Patent No.: US 8,539,962 B2
(45) Date of Patent: Sep. 24, 2013

(54) COSMETIC FOR EYELASHES

(75) Inventors: Takuma Kurahashi, Yokohama (JP); Katsuyuki Kaneko, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 84 days.

(21) Appl. No.: 12/851,635

(22) Filed: Aug. 6, 2010

(65) Prior Publication Data

US 2010/0313906 A1    Dec. 16, 2010

Related U.S. Application Data

(62) Division of application No. 11/794,419, filed as application No. PCT/JP2006/300583 on Jan. 18, 2006, now abandoned.

(30) Foreign Application Priority Data

Jan. 21, 2010   (JP) .................................. 2005-013532

(51) Int. Cl.
*A61K 8/02*    (2006.01)
*A61K 8/27*    (2006.01)
*A61Q 1/10*    (2006.01)

(52) U.S. Cl.
USPC ........................................................ 132/218

(58) Field of Classification Search
None
See application file for complete search history.

(56) References Cited

U.S. PATENT DOCUMENTS

| 6,669,389 B2 * | 12/2003 | Gueret ........................... 401/122 |
| 2003/0086951 A9 * | 5/2003 | Piot et al. ....................... 424/401 |
| 2003/0150077 A1 * | 8/2003 | Montoli et al. ................. 15/206 |
| 2004/0040567 A1 * | 3/2004 | Rousselet ...................... 132/218 |

OTHER PUBLICATIONS

Japanese Patent Document No. 2004-107237 (English Translation).*
Japanese Patent Document No. 2004-269493 (English Translation).*

* cited by examiner

*Primary Examiner* — Robert A Wax
*Assistant Examiner* — Randeep Singh
(74) *Attorney, Agent, or Firm* — Andrew F. Young, Esq.; Lackenbach Siegel, LLP

(57) ABSTRACT

The present invention is a cosmetic for eyelashes characteristically comprising modified cross-section hollow fibers. What is preferable is a cosmetic for eyelashes characteristically containing said modified cross-section hollow fibers that are polygonal cross-section hollow fibers having depressions so they can orient along the eyelashes wherein the length of the hollow fibers is 0.5-4 mm and the size is 20-50 μm.

The object of the present invention is to provide a cosmetic for eyelashes that exhibits a superior curling effect and long lash effect and allows a beautiful finish.

18 Claims, 3 Drawing Sheets

COSMETIC FOR EYELASHES

CROSS REFERENCE TO A RELATED APPLICATIONS

This is a divisional patent application of application Ser. No. 11/794,419 filed Jun. 27, 2007, now abandoned.

TECHNICAL FIELD

The present invention related to a cosmetic for eyelashes that is used as mascara and such. More specifically it is related to a cosmetic for eyelashes containing modified cross-section hollow fibers.

BACKGROUND ART

Conventionally, cosmetics for eyelashes containing fibers, natural fibers and/or synthetic fibers, for the purpose of making eyelashes look longer (long lash effect) have been used.

However, it is difficult to obtain a sufficient long lash effect simply by adding fibers to a cosmetic for eyelashes. Also, the curling effect is hard to achieve. Therefore, surface treatments of fibers have been investigated (see Patent Citation 1 for example). Furthermore, investigations have been carried out on blending in fibers having forms that facilitate orienting along eyelashes, utilizing fibers having modified cross-sections (see Patent Citation 2).

For cosmetics for eyelashes that aim at increasing the volume of eyelashes, investigations have been carried out about blending in fibers with waves (see Patent Citation 3, for example).

However, even the cosmetics for eyelashes containing surface-treated fibers and/or wave fibers are applied to eyelashes, each fiber's orientation is random and not in line with others. That is, the fibers attach to eyelashes sideways and cannot achieve natural looking eyelashes.

On the other hand, the use of modified cross-section fibers can achieve natural looking eyelashes. However, a reduction in the curling effect is inevitable.

Various patent applications have been filed about manufacturing methods of modified cross-section fibers (see Patent Citation 4 and Patent Citation 5). Hollow fibers have been developed as hollow threads for swimsuits (see p 156-157 in Non-Patent Citation 1, for example), but have never been used for cosmetics for eyelashes.

Patent Citation 1: Japanese Patent Laid-Open No. 2002-154932 bulletin
Patent Citation 2: Japanese Patent Laid-Open No. 2004-107237 bulletin
Patent Citation 3: Japanese Patent Laid-Open No. 2002-308735 bulletin
Patent Citation 4: Japanese Patent Laid-Open H05-132812 bulletin
Patent Citation 5: Japanese Patent Publication H04-033893
Non Patent Citation 1: Haiteku Sen-i no Sekai (World of Hightech Fibers): written by Motomiya, Tatsuya, published by Nikkan Kogyo Shinbun

DISCLOSURE OF INVENTION

Technical Problem

The present invention has been carried out in view of the aforementioned situation and its technological object is to provide a cosmetic for eyelashes wherein, when applied on eyelashes, the fibers line up in the direction of the eyelashes and adhere securely to the eyelashes without falling off, said cosmetic also having a superior long lash effect, i.e. the effect of making eyelashes look longer, and being capable of giving a curling effect.

The inventors conducted earnest research based on the aforementioned views and discovered that adding hollow fibers having modified cross-sections that are different from round or oval shapes, rather than adding fibers having round cross-sections the same as that of eyelashes, surprisingly achieves the aforementioned object, thus completing the present invention.

Technical Solution

That is, the present invention provides a cosmetic for eyelashes characteristically comprising modified cross-section hollow fibers.

Also, the present invention provides the aforementioned cosmetic for eyelashes characteristically comprising said modified cross-section hollow fibers that are polygonal cross-section hollow fibers having depressions so they can orient along the eyelashes wherein the length of the hollow fibers is 0.5-4 mm and the size is 20-50 μm.

Furthermore, the present invention provides the aforementioned cosmetic for eyelashes wherein each side of the polygonal cross-section of said polygonal cross-section hollow fibers is depressed like an arch.

Also, the present invention provides the aforementioned cosmetic for eyelashes wherein the cross-section of said polygonal cross-section hollow fibers is a triangle, tetragon, or pentagon.

Advantageous Effects

The present invention can provide a cosmetic for eyelashes wherein, when applied on eyelashes, the fibers line up in the direction of the eyelashes and adhere securely to the eyelashes without falling off, said cosmetic also having a superior long lash effect, i.e. the effect of making eyelashes look longer, and being capable of giving a superior curling effect.

BEST MODE FOR CARRYING OUT THE INVENTION

The present invention is described in detail below.

Figure 1:
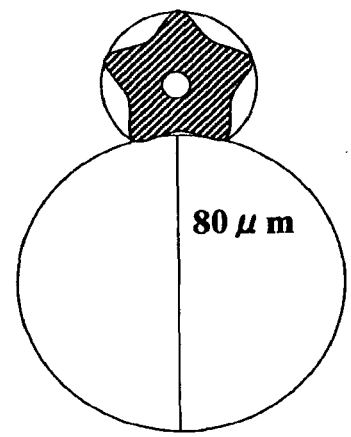
FIG. 1 is a cross-sectional view showing a hollow fiber having a pentagonal modified cross-section oriented along an eyelash.
Figure 2:
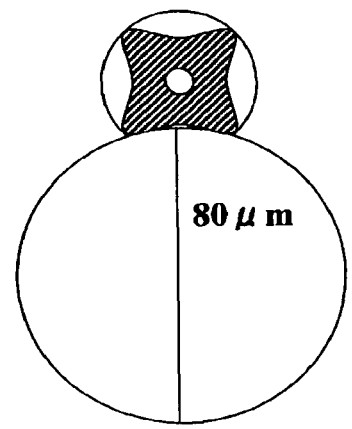
FIG. 2 is a cross-sectional view showing a hollow fiber having a tetragonal modified cross-section oriented along an eyelash.
Figure 3:
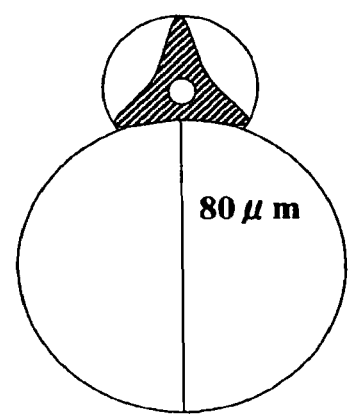
FIG. 3 is a cross-sectional view showing a hollow fiber having a triangular modified cross-section oriented along an eyelash.
Figure 4:
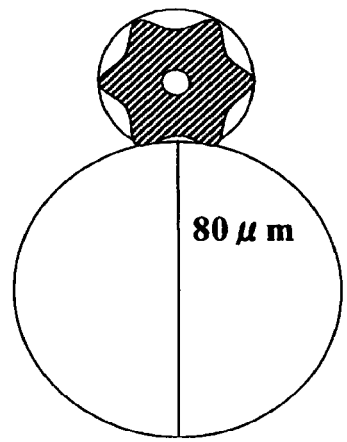
FIG. 4 is a cross-sectional view showing a hollow fiber having a hexagonal modified cross-section oriented along an eyelash.
Figure 5:
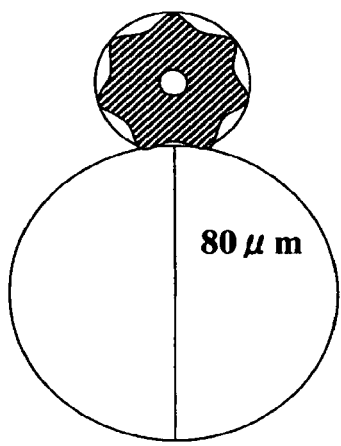
FIG. 5 is a cross-sectional view showing a hollow fiber having a heptagonal modified cross-section oriented along an eyelash.
Figure 6:
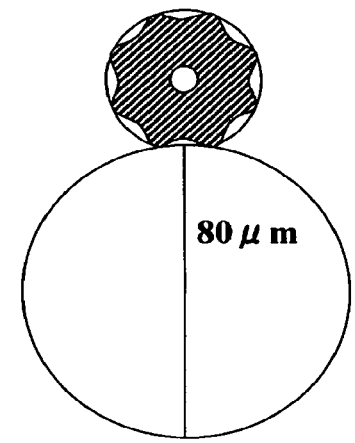
FIG. 6 is a cross-sectional view showing a hollow fiber having an octagonal modified cross-section oriented along an eyelash.
Figure 7:
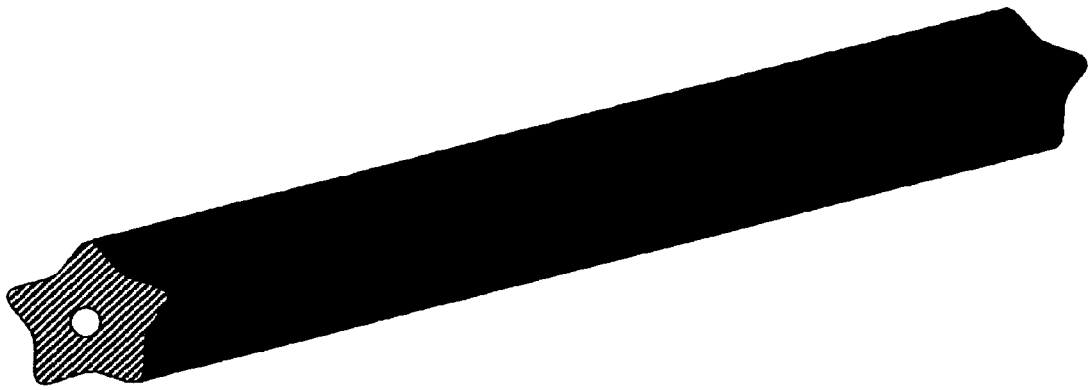
FIG. 7 is a partial perspective view of a hollow fiber having a pentagonal modified cross-section.
Figure 8:
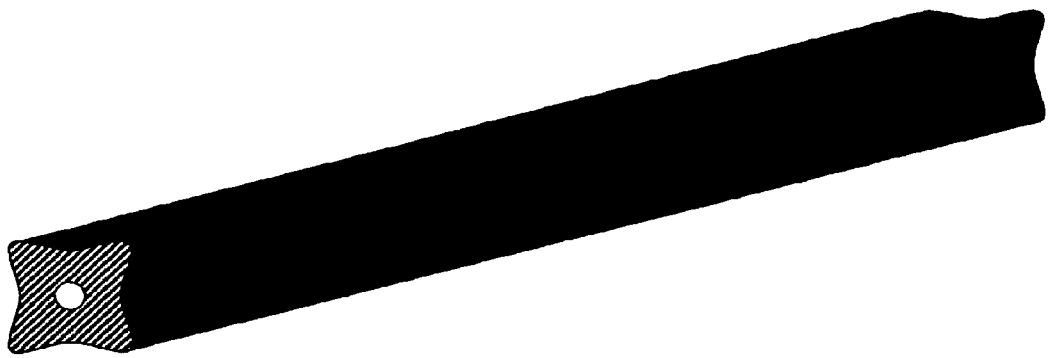
FIG. 8 is a partial perspective view of a hollow fiber having a tetragonal modified cross-section.
Figure 9:
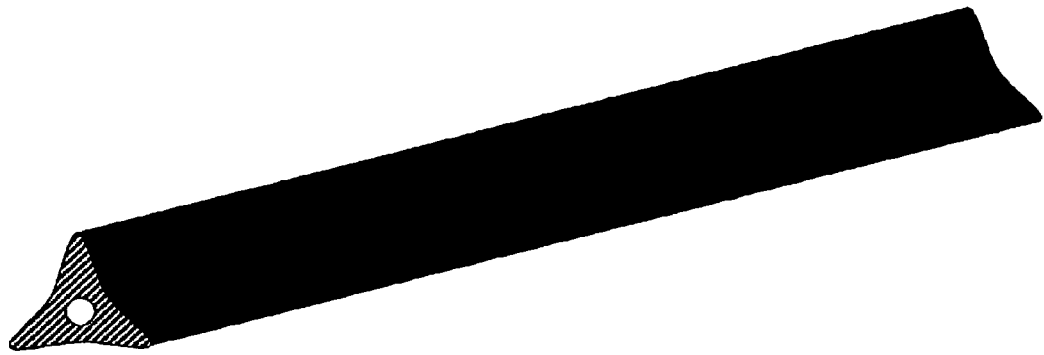
FIG. 9 is a partial perspective view of a hollow fiber having a triangular modified cross-section.

The modified cross-section hollow fibers used in the present invention are those having a cross-section of the fiber other than round or oval. These fibers have a specific cross-section such as a triangle, tetragon, pentagon, or polygon, and the inside is continuously hollow. Preferable fibers are those that have depressions on the circumference of the cross-section (sides that connect peaks) that allow them to be oriented along the eyelash. Specifically, they have the cross-sections shown in FIGS. 1-6. Particularly preferable are hollow fibers having a modified cross-section that is triangular (FIG. 3), tetragonal (FIG. 2), or pentagonal (FIG. 1); the most preferable are pentagonal (FIG. 1) modified cross-section hollow fibers. FIGS. 7-9 are perspective views of hollow fibers having pentagonal, tetragonal, and triangular modified cross-sections (each figure is a partial perspective view of a length of a fiber; a part of a side of the fiber is painted black).

The depression that can be oriented along the eyelash should preferably be an arch-shaped depression along each side of the polygonal cross-section. This depression dramatically improves the orientation of the modified cross-section hollow fibers (i.e. the attached fibers are oriented along the eyelash), and therefore improves the long lash effect. Also, the tendency for the fibers to attach to the eyelash in the transverse orientation is suppressed, which dramatically improves the finished appearance.

In FIGS. 1-6, the eyelash is represented as a round cross-section having a diameter of 80 µm. These figures illustrate how the modified cross-section hollow fibers are oriented along this eyelash. The hollow part of the hollow fiber is the white area in the black background. The cross-sectional shape of this hollow part is not limited in particular; a round shape as shown in each figure is preferable.

The material of the fiber is not limited as long as it is a synthetic fiber that can be made hollow. Specific examples include synthetic fibers such as nylon, polyester, polypropylene, rayon, cupra, acetate, triacetate, acryl, polyurethane, vinylon, promix, pinilon, and polynosic. Particularly preferable fiber materials include nylon and polyester.

The modified cross-section hollow fibers used in the present invention can be manufactured by spinning synthetic fibers by using a spinneret designed to have a freely chosen shape; they can be manufactured by using a prior art method. A modified cross-section hollow fiber by itself is not a new fiber; however, using it in a cosmetic for eyelashes is an epoch making invention particularly from the point of view of the effects of the present invention. The degree of hollowness (hollow ratio) is preferably about 10% from the point of view of designing the spinneret. Selection of the hollow structure is not limited.

The length of the modified cross-section hollow fibers is preferably 0.5-4 mm, and more preferably 2-3 mm. If it is less than 0.5 mm, then the effect of making the eyelashes look longer is insufficient. If it is longer than 4 mm, then natural looking eyelashes are hard to obtain and cosmetics for eyelashes containing such fibers are harder to apply.

It should be noted that those having a triangular, tetragonal, or pentagon cross-section have a superior long lash effect when the length is 2-3 mm, rather than 4 mm; the most preferable length is about 2 mm.

The size of the modified cross-section fibers is preferably 20-50 µm, more preferably 30-40 µm. If it is less than 20 µm, then the fibers lack tenacity and cannot be oriented along the eyelashes easily, exhibiting an insufficient effect to make eyelashes look longer; if it is more than 50 µm, then it is difficult to have natural looking eyelashes and cosmetics containing such fibers are harder to apply because they don't easily attach to a brush or an eyelash. The most preferable are pentagonal modified cross-section fibers having a size of 40 µm.

A size of a modified cross-section fiber is defined as the diameter of a circle circumscribing the cross-section of the fiber. In FIGS. 1-6, circles circumscribing the modified cross-section fibers shown with hatched lines are indicated with solid lines.

The content of the modified cross-section fibers is preferably 0.5-8 wt %, more preferably 1-7 wt %, of the total amount of the cosmetic for eyelashes. If it is less than 0.5 wt %, then the effect of making the eyelashes look longer is insufficient. If it is more than 8.0 wt %, then natural looking eyelashes are hard to obtain and cosmetics for eyelashes containing such fibers are harder to apply.

The modified cross-section fibers can be dyed to any color. Also, various surface treatments can be done as necessary.

It is preferable to add wax to the cosmetic for eyelashes of the present invention. Wax means an oil component that is solid at ordinary temperatures. Specific examples include beeswax, candelilla wax, cotton wax, carnauba wax, bayberry wax, tree wax, whale wax, montan wax, bran wax, lanolin, kapok wax, Japanese core wax, lanolin acetate, liquid lanolin, sugar cane wax, lanolin fatty acid isopropyl ester, hexyl laurate, reduced lanolin, jojoba wax, hard lanolin, shellac wax, bees wax, microcrystalline wax, paraffin wax, POE lanolin alcohol ether, POE lanolin alcohol acetate, POE cholesterol ether, lanolin fatty acid polyethylene glycol, fatty acid glyceride, hydrogenated castor oil, petrolatum, POE hydrogenated lanolin ethyl alcohol ether, alkyl silicone, and jojoba ester. One, two or more kinds of these waxes are selected for use.

The blend ratio of the wax in the cosmetic for eyelashes is adjusted as appropriate; it is preferably 1-30 wt %, more preferably 5-25 wt %.

If the blend ratio is less than 1 wt %, then the effect of the present invention may not be manifested sufficiently. On the other hand, if the blend ratio is more than 30 wt %, then the long lasting coverage of the cosmetic becomes poor. Also, stickiness and hardness increase and therefore the cosmetic becomes harder to apply.

It is preferable to add a film forming resin to the cosmetic for eyelashes of the present invention. Specific examples for use include latexes such as polyvinyl alcohol, polyvinyl pyrrolidone, polyvinyl acetate, and polyalkyl acrylic acid, cellulose derivatives such as dextrin, alkyl cellulose, and nitrocellulose, and silicone resins such as trimethylsiloxysilicic acid, trimethylsiloxysilylpropylcarbamic acid, fluorine-modified silicone, and acryl silicone. One, two or more kinds of these resins are selected for use. Of these, trimethylsiloxysilicic acid is particularly preferable. Commercially available products that can be used include KF7312J and X-21-5250 (both from Shin-Etsu Silicone Co., Ltd.).

The blend ratio of the film forming resin (solid) in the cosmetic for eyelashes is adjusted as appropriate; it is preferably 1-25.0 wt %, and more preferably 2.0-20 wt %. If the blend ratio is less than 0.1 wt %, then the curl-maintaining effect may decrease and secondary adhesion between fibers may occur. Also, in terms of adhesion of the fibers, if the amount of the film forming resin is small, then the fibers may fall off. On the other hand, if the blend ratio is more than 25.0 wt %, then the cosmetic becomes harder to apply, which is not preferable.

It is preferable to add a coloring material to the present invention. Selection of the coloring material is not limited as long as it is used for makeup cosmetics in general. Examples include inorganic pigments such as talc, mica, kaolin, calcium carbonate, zinc flower, titanium dioxide, red iron oxide, yellow iron oxide, black iron oxide, ultramarine blue, Berlin blue, carbon black, lower titanium oxide, cobalt violet, chromium oxide, chromium hydroxide, cobalt titanate, bismuth oxychloride, and titanium-mica type pearl pigment; and organic pigments such as barium or aluminum rake including red 201, red 202, red 204, red 205, red 220, red 226, red 228, red 405, orange 203, yellow 205, yellow 4, yellow 5, blue 1, blue 404, and green 3, and natural pigments/dyes such as chlorophyll and β-carotene. One, two, or more types of these coloring materials can be used.

The blend ratio of the coloring material is adjusted as appropriate. It is preferably 0.1-30 wt %, and more preferably 3-20 wt %. A blend ratio over 30 wt % would not be preferable in view of adhesion. If it is less than 0.1 wt %, then the effect of the coloring material may not be sufficient.

It is preferable to add a thickener to the cosmetic for eyelashes of the present invention since this provides a means to adjust the viscosity. Examples of the thickener include dextrin fatty acid ester, bentonite, xanthan gum, and cellulose gum. One, two or more kinds of these thickeners are selected for use.

The blend ratio of the thickener is adjusted as appropriate for the desired viscosity. It is preferably 0.1-30 wt %, more preferably 1-20 wt %. If the blend ratio is less than 0.1 wt %, then obtaining a sufficient hardness may be difficult. On the other hand, if the blend ratio is more than 30 wt %, then the hardness may be too high and smoothness may be lost.

In the present invention, a conventional method can be used to blend the aforementioned ingredients to prepare a cosmetic for eyelashes. Ingredients that can usually be blended into makeup cosmetics can be added within a quantitative and/or qualitative range that does not adversely affect the effects of the present invention. Examples of such ingredients include alcohols, polyhydric alcohols, drugs, surfactants, water soluble polymers, clay minerals, powders, preservatives, perfumes, antioxidants, ultraviolet absorbents, humectants, fats and oils, and oil based ingredients such as hydrocarbon oils.

EXAMPLES

The invention is described in specific detail through Examples. The present invention is not limited to these Examples. The blend ratios in the recipes are in relation to the total amount and in mass-percentage units unless specified otherwise.

"Modified Cross-Section Hollow Fibers"

The modified cross-section hollow fibers used in Examples were prepared with a conventional method by spinning nylon to have pentagonal (cross-section shape of FIG. 1), tetragonal (cross-section shape of FIG. 2), and triangle (cross-section shape of FIG. 3) cross-sections. The hollow ratio is approximately 10%. Nylon fibers, each having a length of 0.5 mm, 1 mm, 2 mm, 3 mm, or 4 mm and a size of 30 μm or 40 μm were blended into the cosmetics for eyelashes of the present invention.

For Comparative examples, solid (non-hollow) fibers having a round cross-section and those having a triangular cross-section were used. Each of the solid cross-section fibers in Comparative examples has a length of 2 mm and a size of 30 μm, made of nylon.

"Evaluation Method"

(1) Curling Effect 20 specialized panelists applied the cosmetic for eyelashes (mascara) on their eyelashes 10 times, observed them with the naked eye; and evaluation was conducted based on the following criteria.

⊚: 16 or more of the 20 reported there was a curling effect.
○: 9-15 of the 20 reported there was a curling effect.
Δ: 5-8 of the 20 reported there was a curling effect.
X: 4 or less of the 20 reported there was a curling effect.

(2) Long Lash Effect 20 specialized panelists applied the cosmetic for eyelashes (mascara) on their eyelashes 10 times and observed the length of the eyelashes before and after the application with a microscope; evaluation was done based on the relative length of the eyelashes. The values are shown in a table.

(3) Appearance of the Finish (Degree of the Fibers' Orientation in the Direction of the Eyelashes)

20 specialized panelists applied the cosmetic for eyelashes (mascara) on their eyelashes 10 times and observed the length of the eyelashes after the application; evaluation was conducted by counting the fibers protruding from the eyelashes. The values are shown in a table. The smaller the number, the better the finish.

Mascaras containing the aforementioned fibers were prepared with a conventional method and the (1) curling effect, (2) long lash effect, and (3) appearance of the finish (degree of the fibers' orientation in the direction of the eyelashes) were evaluated. For Comparative examples, mascara containing non-hollow round cross-section solid fibers (Comparative example 1) and mascara containing triangular cross-section solid fibers (Comparative example 2) were evaluated for the aforementioned effects. The recipes of the mascaras (wt %) and results are shown in Table 1.

Examples 1-9 and Comparative Examples 1-3

In Table 1, the length, size, and cross-section shape of the nylon fibers are shown. For example, the mascara in Example 2 is shown to be using triangular cross-section hollow nylon fibers having a length of 1 mm and a size of 40 μm. Also, Comparative example 2 is shown to be using round cross-section solid nylon fibers having a length of 2 mm and a size of 30 μm.

TABLE 1

| Ingredient names | Example 1 | Example 2 | Example 3 | Example 4 | Example 5 | Example 6 | Example 7 | Example 8 | Example 9 | Comparative example 1 | Comparative example 2 | Comparative example 3 |
|---|---|---|---|---|---|---|---|---|---|---|---|---|
| Light isoparaffin | To 100 | To 100 | To 100 | To 100 | To 100 | To 100 | To 100 | To 100 | To 100 | To 100 | To 100 | To 100 |
| Decamethylcyclopenta-siloxane | 20.0 | 20.0 | 20.0 | 20.0 | 20.0 | 20.0 | 20.0 | 20.0 | 20.0 | 20.0 | 20.0 | 20.0 |
| Microcrystalline wax | 17.0 | 17.0 | 17.0 | 17.0 | 17.0 | 17.0 | 17.0 | 17.0 | 17.0 | 17.0 | 17.0 | 17.0 |
| Trimethylsiloxysilicic acid | 11.0 | 11.0 | 11.0 | 11.0 | 11.0 | 11.0 | 11.0 | 11.0 | 11.0 | 11.0 | 11.0 | 11.0 |

TABLE 1-continued

| Ingredient names | Example 1 | Example 2 | Example 3 | Example 4 | Example 5 | Example 6 | Example 7 | Example 8 | Example 9 | Comparative example 1 | Comparative example 2 | Comparative example 3 |
|---|---|---|---|---|---|---|---|---|---|---|---|---|
| Black iron oxide | 5.0 | 5.0 | 5.0 | 5.0 | 5.0 | 5.0 | 5.0 | 5.0 | 5.0 | 5.0 | 5.0 | 5.0 |
| Dextrin fatty acid ester | 15.0 | 15.0 | 15.0 | 15.0 | 15.0 | 15.0 | 15.0 | 15.0 | 15.0 | 15.0 | 15.0 | 15.0 |
| Nylon fiber 0.5 mm-40 μm (triangular hollow) | 4.0 | — | — | — | — | — | — | — | — | — | — | — |
| Nylon fiber 1 mm-40 μm (triangular hollow) | — | 4.0 | — | — | — | — | — | — | — | — | — | — |
| Nylon fiber 2 mm-30 μm (triangular hollow) | — | — | 4.0 | — | — | — | — | — | — | — | — | — |
| Nylon fiber 2 mm-40 μm (triangular hollow) | — | — | — | 4.0 | — | — | — | — | — | — | — | — |
| Nylon fiber 2 mm-30 μm (tetragonal hollow) | — | — | — | — | 4.0 | — | — | — | — | — | — | — |
| Nylon fiber 2 mm-30 μm (pentagonal hollow) | — | — | — | — | — | 4.0 | — | — | — | — | — | — |
| Nylon fiber 2 mm-40 μm (pentagonal hollow) | — | — | — | — | — | — | 4.0 | — | — | — | — | — |
| Nylon fiber 3 mm-40 μm (pentagonal hollow) | — | — | — | — | — | — | — | 4.0 | — | — | — | — |
| Nylon fiber 4 mm-40 μm (triangular hollow) | — | — | — | — | — | — | — | — | 4.0 | — | — | — |
| Nylon fiber 0.3 mm-2 μm (round solid) | — | — | — | — | — | — | — | — | — | 4.0 | — | — |
| Nylon fiber 2 mm-30 μm (round solid) | — | — | — | — | — | — | — | — | — | — | 4.0 | — |
| Nylon fiber 2 mm-30 μm (triangular solid) | — | — | — | — | — | — | — | — | — | — | — | 4.0 |
| Curling effect | ◎ | ◎ | ◎ | ◎ | ◎ | ◎ | ◎ | ◎ | ◎ | Δ | Δ | Δ |
| Long effect (ratio before and after application, based on image analysis) | 1.045 | 1.048 | 1.053 | 1.076 | 1.073 | 1.089 | 1.105 | 1.056 | 1.048 | 1.020 | 1.042 | 1.048 |
| Finish (number of fibers protruding from the eyelash) | 60 | 52 | 27.3 | 23.3 | 29 | 37 | 24.7 | 37.3 | 36.3 | 70 | 40.7 | 37.3 |

The results of Comparative examples 1-3 indicate that changing from the round cross-section solid fibers to the triangular cross-section solid fibers improves the long effect and the appearance of the finish, but the curling effect stayed at a similar low level for both.

On the contrary, Examples using hollow fibers exhibit a substantially improved curling effect compared with Comparative examples. Also, the appearance of the finish substantially improves compared with the round cross-section solid fibers of Comparative example 2 and the triangular cross-section solid fibers of Comparative example 3 (Comparative example 3: 37.3→Example 3: 27.3); furthermore, the long lash effect recognizably improves as well (Comparative example 3: 1.048→Example 3: 1.053). The long lash effect is particularly prominent when the length is 2-3 mm. The appearance of the finish is particularly good when the length is 2-4 mm.

The above results indicate that the cosmetic for eyelashes of the present invention that contains modified cross-section hollow fibers exhibits a particularly prominent curling effect and also provide an excellent long lash effect and appearance of the finish, compared with cosmetics for eyelashes containing non-hollow round solid fibers or modified cross-section fibers.

Examples of the cosmetic for eyelashes of the present invention are shown in Tables 2-4. Each of them is a cosmetic for eyelashes that, when applied on the eyelashes, provides a beautiful finish by suppressing the fibers from sticking out from the eyelash in random directions, securely adheres to the eyelashes without having fibers fall off, exhibits the superior long lash effect of making eye lashes look longer, and exhibits an excellent curling effect.

Water-in-Oil Type Mascara

TABLE 2

| Ingredient names | Example 10 | Example 11 | Example 12 | Example 13 | Example 14 | Example 15 | Example 16 | Example 17 | Example 18 | Example 19 | Example 20 |
|---|---|---|---|---|---|---|---|---|---|---|---|
| Light isoparaffin | 8 | 8 | 8 | 8 | 8 | 8 | 8 | 8 | 8 | 8 | 8 |
| Dimethylpolysiloxane | 3 | 3 | 3 | 3 | 3 | 3 | 3 | 3 | 3 | 3 | 3 |
| Decamethylcyclopentasiloxane | 10 | 10 | 10 | 10 | 10 | 10 | 10 | 10 | 10 | 10 | 10 |
| Trimethylsiloxysilicic acid | 10 | 10 | 10 | 10 | 10 | 10 | 10 | 10 | 10 | 10 | 10 |
| Methylpolysiloxane emulsion | AA* | AA* | AA* | AA* | AA* | AA* | AA* | AA* | AA* | AA* | AA* |
| 1,3-butylene glycol | 4 | 4 | 4 | 4 | 4 | 4 | 4 | 4 | 4 | 4 | 4 |
| Polyethylene glycol dioleate | 2 | 2 | 2 | 2 | 2 | 2 | 2 | 2 | 2 | 2 | 2 |
| Diglyceryl diisostearate | 2 | 2 | 2 | 2 | 2 | 2 | 2 | 2 | 2 | 2 | 2 |
| Sodium hydrogen carbonate | 0.1 | 0.1 | 0.1 | 0.1 | 0.1 | 0.1 | 0.1 | 0.1 | 0.1 | 0.1 | 0.1 |
| Sodium metaphosphate | AA* | AA* | AA* | AA* | AA* | AA* | AA* | AA* | AA* | AA* | AA* |
| DL-α-tocopherol acetate | 0.1 | 0.1 | 0.1 | 0.1 | 0.1 | 0.1 | 1.1 | 1.1 | 2.1 | 3.1 | 4.1 |
| p-oxybenzoic ester | AA* | AA* | AA* | AA* | AA* | AA* | AA* | AA* | AA* | AA* | AA* |

TABLE 2-continued

| Ingredient names | Example 10 | Example 11 | Example 12 | Example 13 | Example 14 | Example 15 | Example 16 | Example 17 | Example 18 | Example 19 | Example 20 |
|---|---|---|---|---|---|---|---|---|---|---|---|
| Sodium dehydroacetate | AA* | AA* | AA* | AA* | AA* | AA* | AA* | AAA | AA* | AA* | AA* |
| Black iron oxide | 7 | 7 | 7 | 7 | 7 | 7 | 7 | 7 | 7 | 7 | 7 |
| Sea weed extract | 0.1 | 0.1 | 0.1 | 0.1 | 0.1 | 0.1 | 0.1 | 0.1 | 0.1 | 0.1 | 0.1 |
| Bentonite | 1 | 1 | 1 | 1 | 1 | 1 | 1 | 1 | 1 | 1 | 1 |
| Dimethyldistearyl ammonium hectorite | 5 | 5 | 5 | 5 | 5 | 5 | 5 | 5 | 5 | 5 | 5 |
| Polyvinyl acetate emulsion | 20 | 20 | 20 | 20 | 20 | 20 | 20 | 20 | 20 | 20 | 20 |
| Heavy liquid paraffin | 4 | 4 | 4 | 4 | 4 | 4 | 4 | 4 | 4 | 4 | 4 |
| Purified water | To 100 | To 100 | To 100 | To 100 | To 100 | To 100 | To 100 | To 100 | To 100 | To 100 | To 100 |
| Nylon fiber 2 mm-30 μm (triangular hollow) | 3 | | | | | | 1 | | | | |
| Nylon fiber 2 mm-40 μm (triangular hollow) | | 3 | | | | | | | 2 | | |
| Nylon fiber 2 mm-30 μm (tetragonal hollow) | | | 3 | | | | | | 2 | | |
| Nylon fiber 2 mm-30 μm (pentagonal hollow) | | | | 3 | | | | | | 2 | |
| Nylon fiber 2 mm-40 μm (pentagonal hollow) | | | | | 3 | | 3 | 2 | 2 | 2 | 3 |
| Nylon fiber 3 mm-40 μm (pentagonal hollow) | | | | | | 3 | | | | | 1 |

AA*: Appropriate amount

Oil-in-Water Type Mascara

TABLE 3

| Ingredient names | Example 21 | Example 22 | Example 23 | Example 24 | Example 25 | Example 26 | Example 27 | Example 28 | Example 29 | Example 30 | Example 31 |
|---|---|---|---|---|---|---|---|---|---|---|---|
| Light isoparaffin | 6 | 6 | 6 | 6 | 6 | 6 | 6 | 6 | 6 | 6 | 6 |
| Dimethylpolysiloxane | 1 | 1 | 1 | 1 | 1 | 1 | 1 | 1 | 1 | 1 | 1 |
| Decamethylcyclopentasiloxane | 5 | 5 | 5 | 5 | 5 | 5 | 5 | 5 | 5 | 5 | 5 |
| Trimethylsiloxysilicic acid | 5 | 5 | 5 | 5 | 5 | 5 | 5 | 5 | 5 | 5 | 5 |
| Methylpolysiloxane emulsion | AA* | AA* | AA* | AA* | AA* | AA* | AA* | AA* | AA* | AA* | AA* |
| Isopropanol | 3 | 3 | 3 | 3 | 3 | 3 | 3 | 3 | 3 | 3 | 3 |
| 1,3-butylene glycol | 6 | 6 | 6 | 6 | 6 | 6 | 6 | 6 | 6 | 6 | 6 |
| Polyoxyethylene hydrogenated castor oil | 1 | 1 | 1 | 1 | 1 | 1 | 1 | 1 | 1 | 1 | 1 |
| Sucrose fatty acid ester; | 0.6 | 0.6 | 0.6 | 0.6 | 0.6 | 0.6 | 0.6 | 0.6 | 0.6 | 0.6 | 0.6 |
| Diglyceryl diisostearate | 1 | 1 | 1 | 1 | 1 | 1 | 1 | 1 | 1 | 1 | 1 |
| Sodium hydrogen carbonate | 0.01 | 0.01 | 0.01 | 0.01 | 0.01 | 0.01 | 0.01 | 0.01 | 0.01 | 0.01 | 0.01 |
| DL-α-tocopherol acetate | 0.1 | 0.1 | 0.1 | 0.1 | 0.1 | 0.1 | 0.1 | 0.1 | 0.1 | 0.1 | 0.1 |
| Sodium acetylated hyaluronate | 0.1 | 0.1 | 0.1 | 0.1 | 0.1 | 0.1 | 0.1 | 0.1 | 0.1 | 0.1 | 0.1 |
| p-oxybenzoic ester | AA* | AA* | AA* | AA* | AA* | AA* | AA* | AA* | AA* | AA* | AA* |
| Phenoxy ethanol | 0.3 | 0.3 | 0.3 | 0.3 | 0.3 | 0.3 | 0.3 | 0.3 | 0.3 | 0.3 | 0.3 |
| Black iron oxide | 8 | 8 | 8 | 8 | 8 | 8 | 8 | 8 | 8 | 8 | 8 |
| Bentonite | 1 | 1 | 1 | 1 | 1 | 1 | 1 | 1 | 1 | 1 | 1 |
| Dimethyldistearyl ammonium hectorite | 4 | 4 | 4 | 4 | 4 | 4 | 4 | 4 | 4 | 4 | 4 |
| Polyvinyl alcohol | 4 | 4 | 4 | 4 | 4 | 4 | 4 | 4 | 4 | 4 | 4 |
| Alkyl acrylate copolymer emulsion | 12 | 12 | 12 | 12 | 12 | 12 | 12 | 12 | 12 | 12 | 12 |
| Polyvinyl acetate emulsion | 12 | 12 | 12 | 12 | 12 | 12 | 12 | 12 | 12 | 12 | 12 |
| Silicic acid anhydride | 0.5 | 0.5 | 0.5 | 0.5 | 0.5 | 0.5 | 0.5 | 0.5 | 0.5 | 0.5 | 0.5 |
| Titanium oxide | 1 | 1 | 1 | 1 | 1 | 1 | 1 | 1 | 1 | 1 | 1 |
| Perfume | AA* | AA* | AA* | AA* | AA* | AA* | AA* | AA* | AA* | AA* | AA* |
| Purified water | To 100 | To 100 | To 100 | To 100 | To 100 | To 100 | To 100 | To 100 | To 100 | To 100 | To 100 |
| Nylon fiber 2 mm-30 μm (triangular hollow) | 6 | | | | | | 2 | | | | |
| Nylon fiber 2 mm-40 μm (triangular hollow) | | 6 | | | | | | | 3 | | |
| Nylon fiber 2 mm-30 μm (tetragonal hollow) | | | 6 | | | | | | 3 | | |
| Nylon fiber 2 mm-30 μm (pentagonal hollow) | | | | 6 | | | | | | 3 | |
| Nylon fiber 2 mm-40 μm (pentagonal hollow) | | | | | 6 | | 4 | 3 | 3 | 3 | 4 |
| Nylon fiber 3 mm-40 μm (pentagonal hollow) | | | | | | 6 | | | | | 2 |

AA*: Appropriate amount

Oil-in-Water Type Mascara Base

TABLE 4

| Ingredient names | Example 32 | Example 33 | Example 34 | Example 35 | Example 36 | Example 37 | Example 38 | Example 39 | Example 40 | Example 41 | Example 42 |
|---|---|---|---|---|---|---|---|---|---|---|---|
| Microcrystalline wax | 10 | 10 | 10 | 10 | 10 | 10 | 10 | 10 | 10 | 10 | 10 |
| Methylpolysiloxane emulsion | AA* | AA* | AA* | AA* | AA* | AA* | AA* | AA* | AA* | AA* | AA* |
| Isopropanol | 3 | 3 | 3 | 3 | 3 | 3 | 3 | 3 | 3 | 3 | 3 |
| 1,3-butylene glycol | 7 | 7 | 7 | 7 | 7 | 7 | 7 | 7 | 7 | 7 | 7 |
| White beeswax | 10 | 10 | 10 | 10 | 10 | 10 | 10 | 10 | 10 | 10 | 10 |
| Sorbitan monostearate | 1 | 1 | 1 | 1 | 1 | 1 | 1 | 1 | 1 | 1 | 1 |
| Polyoxyethylenesorbitan monostearate (20E.0.) | 1 | 1 | 1 | 1 | 1 | 1 | 1 | 1 | 1 | 1 | 1 |
| Isobutylene-sodium malate copolymer solution | 0.1 | 0.1 | 0.1 | 0.1 | 0.1 | 0.1 | 0.1 | 0.1 | 0.1 | 0.1 | 0.1 |
| Talc | 1 | 1 | 1 | 1 | 1 | 1 | 1 | 1 | 1 | 1 | 1 |
| Strong aqueous ammonia | 0.1 | 0.1 | 0.1 | 0.1 | 0.1 | 0.1 | 0.1 | 0.1 | 0.1 | 0.1 | 0.1 |
| p-oxybenzoic ester | AA* | AA* | AA* | AA* | AA* | AA* | AA* | AA* | AA* | AA* | AA* |
| Sea weed extract | 0.1 | 0.1 | 0.1 | 0.1 | 0.1 | 0.1 | 0.1 | 0.1 | 0.1 | 0.1 | 0.1 |
| Aluminum magnesium silicate | 0.7 | 0.7 | 0.7 | 0.7 | 0.7 | 0.7 | 0.7 | 0.7 | 0.7 | 0.7 | 0.7 |
| Alkyl acrylate copolymer emulsion | 22 | 22 | 22 | 22 | 22 | 22 | 22 | 22 | 22 | 22 | 22 |
| Polyvinyl alcohol | 2 | 2 | 2 | 2 | 2 | 2 | 2 | 2 | 2 | 2 | 2 |
| Heavy liquid paraffin | 2 | 2 | 2 | 2 | 2 | 2 | 2 | 2 | 2 | 2 | 2 |
| Purified water | To 100 | To 100 | To 100 | To 100 | To 100 | To 100 | To 100 | To 100 | To 100 | To 100 | To 100 |
| Nylon fiber 2 mm-30 μm (triangular hollow) | 5 | | | | | | | 2 | | | |
| Nylon fiber 2 mm-40 μm (triangular hollow) | | 5 | | | | | | | 3 | | |
| Nylon fiber 2 mm-30 μm (tetragonal hollow) | | | 5 | | | | | | | 3 | |
| Nylon fiber 2 mm-30 μm (pentagonal hollow) | | | | 5 | | | | | | | 3 |
| Nylon fiber 2 mm-40 μm (pentagonal hollow) | | | | | 5 | | 4 | 3 | 3 | 3 | 4 |
| Nylon fiber 3 mm-40 μm (pentagonal hollow) | | | | | | 5 | | | | | 2 |

AA*: Appropriate amount

INDUSTRIAL APPLICABILITY

The cosmetic for eyelashes of the present invention, when applied on the eyelashes, can make eyelashes look natural by suppressing the fibers from orienting in different directions from each other and/or sticking out from the eyelashes in random directions. Furthermore it is a cosmetic for eyelashes having an excellent curling effect.

The invention claimed is:

1. A mascara cosmetic composition for application to eyelashes, said mascara cosmetic composition comprising:
   0.5-8 wt % of hollow fibers having a length of from 0.5-4 mm and a diameter of 20-50 μm, said fibers having a modified pentagonal cross-section represented by a pentagon that allow the hollow fibers to be oriented along an eyelash with each side of said pentagon having an arch shaped depression along each side of the pentagon,
   wherein the mascara cosmetic composition suppresses transverse orientation of said hollow fibers to the eyelashes and facilitates orientation of the hollow fibers along a length of the eyelashes, thereby improving a long lash effect.

2. The mascara cosmetic composition for application to eyelashes of claim 1, wherein said hollow fiber is formed from a synthetic fiber that can be made hollow.

3. The mascara cosmetic composition for application to the eyelashes of claim 1, further comprising 1-30 wt % of a wax.

4. The mascara cosmetic composition for application to the eyelashes of claim 1, further comprising 1-25.0 wt % of a film forming resin.

5. The mascara cosmetic composition for application to the eyelashes of claim 1, further comprising 0.1-30 wt % of a thickener.

6. A mascara cosmetic composition comprising:
   0.5-8 wt % of hollow fibers having a length of from 0.5-4 mm and a diameter of 20-50 μm, said fibers having a modified pentagonal cross-section represented by a pentagon that allow the hollow fibers to be oriented along an eyelash, having an arch-shaped depression along each side thereof;
   1-30 wt % of a wax;
   1-25.0 wt % of a film forming resin; and
   0.1-30 wt % of a thickener,
   wherein said mascara cosmetic composition suppresses transverse orientation of said hollow fibers to the eyelashes when applied thereto, and facilitates orientation of the hollow fibers along a length of the eyelashes, thereby improving a long lash effect.

7. A mascara cosmetic composition for application to eyelashes, said mascara cosmetic composition consisting essentially of:
   0.5-8 wt % of hollow fibers having a length of from 0.5-4 mm and a diameter of 20-50 μm, said fibers having a modified pentagonal cross-section represented by a pentagon that allow the hollow fibers to be oriented along an eyelash, having an arch-shaped depression along each side thereof,
   wherein said mascara cosmetic suppresses transverse orientation of said hollow fibers to the eyelashes, and facilitates orientation of the hollow fibers along a length of the eyelashes, thereby improving a long lash effect.

8. The mascara cosmetic composition of claim 1, wherein the length of the modified cross-section hollow fibers is 2-3 mm.

9. The mascara cosmetic composition of claim 6, wherein the length of the modified cross-section hollow fibers is 2-3 mm.

10. The mascara cosmetic composition of claim 7, wherein the length of the modified cross-section hollow fibers is 2-3 mm.

11. The mascara cosmetic composition of claim 1, wherein the hollow fibers have a diameter of 30-40 μm.

12. The mascara cosmetic composition of claim 6, wherein the hollow fibers have a diameter of 30-40 μm.

13. The mascara cosmetic composition of claim 7, wherein the hollow fibers have a diameter of 30-40 μm.

14. The mascara cosmetic composition of claim 1, further comprising 0.1-30 wt % of a coloring material.

15. The mascara cosmetic composition of claim 6, further comprising 0.1-30 wt % of a coloring material.

16. The mascara cosmetic composition of claim 7, further comprising 0.1-30 wt % of a coloring material.

17. A mascara cosmetic composition comprising:
   3.0-6.0 wt % of hollow fibers having a length of from 2.0-3.0 mm and a diameter of 20-30 μm, said fibers having a pentagonal cross-section represented by a pentagon having an arch shaped depression along each side thereof;
   wherein said mascara cosmetic composition suppresses transverse orientation of said hollow fibers to the eyelashes when applied thereto, and facilitates orientation of the hollow fibers along a length of the eyelashes, thereby improving a long lash effect.

18. The mascara cosmetic composition of claim 17, further comprising:
   1-30 wt % of a wax;
   1-25.0 wt % of a film forming resin;
   0.1-30 wt % of a thickener; and
   0.1-30 wt % of a coloring material.

* * * * *